United States Patent
Roodink et al.

(10) Patent No.: US 6,472,194 B1
(45) Date of Patent: Oct. 29, 2002

(54) PROCESS FOR THE PREPARATION OF THROMBOPLASTIN FROM ANIMAL TISSUE

(75) Inventors: Hendrikus B J Roodink, Twello (NL); Gerjan T van Zeeburg, Eerbeek (NL)

(73) Assignee: Harimex B.V., Loenen (NL)

( * ) Notice: Subject to any disclaimer, the term of this patent is extended or adjusted under 35 U.S.C. 154(b) by 0 days.

(21) Appl. No.: 09/646,836

(22) PCT Filed: Mar. 19, 1999

(86) PCT No.: PCT/NL99/00154

§ 371 (c)(1),
(2), (4) Date: Dec. 4, 2000

(87) PCT Pub. No.: WO99/48922

PCT Pub. Date: Sep. 30, 1999

(30) Foreign Application Priority Data

Mar. 23, 1998 (NL) .............................................. 1008674

(51) Int. Cl.$^7$ ................................................. C12N 9/48
(52) U.S. Cl. ....................................................... 435/212
(58) Field of Search ................................ 530/381, 382; 435/212; 424/94.64

(56) References Cited

U.S. PATENT DOCUMENTS 2,398,077 A * 4/1946 Smith et al.
4,416,812 A * 11/1983 Becker et al.

FOREIGN PATENT DOCUMENTS

SU 1671305 A1 * 8/1991

OTHER PUBLICATIONS

Astrup, T., "Assay and Content of Tissue Thromboplastin in Different Organs" (1965) Thrombosis Diathesis Haemorrhagica, 14, 401–416.*

Østerud et al., "Thromboplastin Content in the Vessel Walls of Different Arteries and Organs of Rabbits" (1986) Thromb. Res., 42(3), 323–329.*

Howell et al., "Comparative Studies on Thromboplastin in Various Tissues and of Factors that Modify its Procoagulant Activity" (1981) Biochem. Soc. Trans., 9(1), 70–71.*

Quick, On the quantitative estimation of prothrombin (1945) American Journal of Clinical Pathology, vol. 15, pp. 560–566.*

Magnusson, Preparation and carbohydrate analysis of bovine prothrombin (1965) Arkiv for Kemi, vol. 23, No. 28, pp. 285–298.*

Chargaff et al., Ultracentrifugation isolation from lung tissue of a macromolecular protein component with thromboplastic properties (1942) J. Biol. Chem., vol. 145, pp. 593–603.*

Fujikata et al. Blood coagulation and clotting tests in carp (1985) Nippon Suisan Gakkaishi, vol. 51, No. 6, pp. 933–939 (abstract only).*

Kuznik et al. Activities of coagulation factor and fibrinolysin in muscles before and after exertion (1975) Voprosy Meditsinskoi Khimii, vol. 21, No. 3, pp. 242–245. (abstract only).*

Eremini, E. L. Hemo coagulating and fibrinolytic properties of muscle tissue in relation to its work regime (1978) Fiziol Zh (Kiev), vol. 24, No. 4, pp. 568–570. (abstract only).*

Kuznetsov, V. I. Distribution of 5'–nucleotidase and thromboplastin activity in human tissues (1983) Kazan. Med. Zh., vol. 64, No. 1, pp. 32–35. (abstract only).*

Smargia Et Al: File Medline, abstract No. 82207075, 1982, XP002089071; "Platelet effect on tissue factor and fibrinolytic inhibition of cultured human fibroblasts and vascular cells", Blood, vol. 60, No. 1, Jul. 1982, pp. 140–147.

Derwent Publications, AB92–388343; XP002089073, "Production of thromboplastin comprises homogeneizing brain and muscle tissues of day–old chicken with distilled water filtration followed by drying", & SU 88 616 530 A (Animals Noncontagious Diseases Research Institute) Aug. 23, 1991.

Golyshenkov: "Blood coagulation, anticoagulant and figrinolytic characteristics of human stomach tissues", Fiziologiya Cheloveka, vol. 22, No. 4, 1996, pp. 114–117, & Biological Abstracts, vol. 1997, abstract No. 107757, XP002089072.

* cited by examiner

Primary Examiner—Jon P. Weber
(74) Attorney, Agent, or Firm—Pillsbury WInthrop LLP

(57) ABSTRACT

The invention relates to a process for the preparation of thromboplastin from animal tissue, using an extraction with an aqueous salt solution, followed by separation of tissue material, in order to obtain a thromboplastin containing solution, wherein muscular tissue obtained from mammals or from fish, is used as the animal tissue. The muscular tissue is directly extracted with an aqueous salt solution.

6 Claims, No Drawings

PROCESS FOR THE PREPARATION OF THROMBOPLASTIN FROM ANIMAL TISSUE

This application is the national phase of international application PCT/NL99/00154 filed Mar. 19, 1999 which designated the U.S.

FIELD OF THE INVENTION

The present invention relates to a process for the preparation of thromboplastin from animal tissue, using an extraction with an aqueous salt solution, followed by separation of tissue material in order to obtain a thromboplastin containing salt solution.

BACKGROUND OF THE INVENTION

An extraction process is known from European patent application EP-A-0 083 773. According to the known process, an acetone powder from the animal tissue, i.e. mammal tissue, particularly brain tissue, is initially prepared. The acetone powder is then extracted with an aqueous salt solution comprising 1–20 mM calcium ions and possibly a surface active substance.

Based on recent scientific research, it appears that using bovine brain tissue and bovine nerve tissue can lead to the transfer of the causative agents of BSE (Bovine Spongiform Encephalitis); (Spongiform Encephalopathy Advisory Committee, September 1994. Transmissible Spongiform Encephalopathies. A Summary of Present Knowledge and Research." HMSO, London, U.K.). Furthermore, it appears that, in order to prepare a satisfactory solution of thromboplastin, first preparing an acetone powder of the relevant tissue, and then carrying out the extraction with a solution of calcium salts and possibly a surface active substance is unnecessary.

SUMMARY OF THE INVENTION

The process according to the invention is characterized in that muscular tissue, obtained from mammals or from fish, is directly extracted with an aqueous salt solution.

The process according to the present invention is characterised in that muscular tissue, obtained from mammals or from fish, is directly extracted with an aqueous salt solution. Smariga, P. E. and Maynard, J. R. (1982) Blood, 60, 140–147 relates to the effects of platelets on the tissue factor and the fibrinolytic inhibition of cultured human fibroblasts and vascular cells. From Derwent Abstract AN 92-388343-XP002089073 relating to SU 88 616 530 A, a process for the preparation of thromboplastin from brain tissue-containing pieces of tissue from 24 hours of chickens is known. Biological Abstracts (1997) 1997, no. 107757 relates to the presence of thromboplastin activity in human gastric tissues.

By using the present process, the BSE problem can be avoided. Moreover, a more simple and less laborious preparation method is obtained, since, according to the invention, the step of preparing an aceton powder is unnecessary. The muscular tissue is simply reduced to smaller pieces and is then extracted. A salt solution without calcium ions or a surface active substance is sufficient.

The muscular tissue which is used is preferably derived from mammals, especially from bovine species, as said muscular tissue can be obtained in large amounts. The process can also be applied advantageously to muscular tissue from fish.

It was experimentally demonstrated that the used muscular tissue is preferably not derived from a freshly slaughtered animal, but that it has an "age" of 4–7 days. Extracts from such an "aged" muscular tissue have a higher thromboplastin activity. A higher thromboplastin activity is also obtained with vacuum packed muscular tissue with an age of 2 weeks.

Concerning the composition of the aqueous salt solution to be used for extracting, it is preferred that it is buffered to a pH value of 6.0–7.5. Using a phosphate salt is particularly preferable, as said salt also has a good buffering action.

During the preparation according to the invention a temperature of 0–4° C. is maintained and principle. However, a higher yield of thromboplastin activity is obtained if the extraction is carried out with salt solution at a temperature of 40–50° C.

The separation of the tissue material following the extraction is preferably carried out by centrifugation. Other separation methods lead to losses and/or are more time-consuming. Thus, filtration leads to losses by adsorption of, for instance, phospholipids, if a paper filter is used, and to higher costs if synthetic filters with a special composition and a particular molecular weight threshold is used in pressurized filtration devices.

The thromboplastin obtained by using the process according to the present invention can for instance be used for nutritional purposes. For such an application, the extraction has to be carried out with a solution of salts which are authorised for nutritional products, such as cooking salt, phosphates and acetates. Concerning an application in meat products, the thromboplastin is of course preferably derived from the same animal species as the species of the meat itself.

DETAILED DESCRIPTION OF THE PREFERRED EMBODIMENTS

The present invention is further illustrated by examples.

EXAMPLE 1

An amount of 100 g of bovine muscular tissue, in the present case shoulder meat, with an age of 5 days was cut down into pieces of approximately 1 cm$^3$, at 4° C. An amount of 400 g of a solution of 150 mM cooking salt (8.77 g/l NaCl in water) was added, also at 4° C. The pieces of meat were homogenized at 11,000–13,000 revolutions per minute, during 1 minute, using a homogenizer. The homogenate was then centrifuged during 30 minutes at 3,200 g, at a temperature of 0° C. From the amount of 500 g homogenate, an amount of 225 g supernatant with a protein content of 20 mg/ml was recovered. The supernatant contained thromboplastin.

The thromboplastin activity was determined by adding the supernatant to a solution of prothrombin and, following a given reaction time, measuring the activity of the formed thrombin. To an amount of 10 ml prothrombin solution (390 NIH-U/ml), an amount of 50 ml of 20 mM Tris-HCl, pH 6.5, 1 ml of 3 M $CaCl_2$ and 250 µl of the thromboplastin solution to be determined was added. Finally, the combination was adjusted to a volume of 100 ml with 20 mM Tris-HCl, pH 6.5. The reaction mixture was incubated during 60 minutes at 25° C. The activity of the obtained thrombin was measured conventionally, using a chromogene substrate (0.1 mM S-2238 from Chromogenix, and in this connection, reference is made to e.g. Hemker H. C. (1983) Handbook of Synthetic Substrates, Chapter IV, Martinus Nijhoff Publishers, Boston). These measurements were also carried out with 250 µl of a supernatant of brain tissue as a positive control. Finally, the thromboplastin activity of the supernatant from muscular tissue from the shoulder was expressed as the percentage of the activity of the supernatant from brain tissue (%RTP). The obtained %RTP value for the supernatant from muscular tissue from the shoulder of bovine animals was 28.

The preparation was repeated with 150 mM sodium phosphate buffer, pH 7.0 (17.37 g/l $Na_2HPO_4.2H_2O$ and 8.19 g/l $NaH_2PO_4.2H_2O$ in water) and with 150 mM acetate buffer (adjusted to pH 7.0 with acetic acid). The activity obtained when using the buffered salt solutions was considerably higher than the activity obtained when using NaCl and the %RTP value was 64.

Comparable results were obtained when the preparations as described above were applied to shoulder tissue of pigs. By homogenising and extracting in 150 mM NaCl, a %RTP value of 24 was obtained. When using the 150 mM sodium phosphate buffer, pH 7.0, a %RTP value of 60 was obtained.

EXAMPLE 2

The influence of the pH value of the extraction solution was investigated using phosphate buffers of 150 mM $NaH_2PO_4/Na_2HPO_4$ with different pH-values. The cutting down into pieces, extractions and determinations with the thromboplastin activity were carried out as described in Example I. The obtained results are summarised in the following Table 1.

TABLE 1

| pH value during extraction | Thromboplastin activity (% RTP) |
|---|---|
| 5.0 | 56.7 |
| 6.0 | 58.8 |
| 6.5 | 65.0 |
| 7.0 | 62.5 |
| 7.5 | 61.1 |

When extracted with buffers adjusted to pH 8.0 and pH 8.5, the homogenate was very viscous and hardly. any pellet could be obtained. From these experiments, it follows that the best results are obtained at a pH value of 6.0–7.5.

EXAMPLE 3

The influence of the age (the time following the slaughtering) of the muscular tissue on the amount of extracted thromboplastin activity was investigated by cutting down an amount of 100 g of muscular tissue from bovine shoulder meat and extracting it as described in Example 1, using a 150 mM sodium phosphate buffer, pH 7.0. The measurement of thromboplastin activity was carried out as described in Example 1. In the following Table 2, the obtained results are summarised.

TABLE 2

| Age/time following slaughtering (days) | Thromboplastin activity (% RTP) |
|---|---|
| 3 | 63.7 |
| 5 | 78.2 |
| 7 | 68.7 |
| 10 | 67.6 |

Based on these results, it appears that the highest thromboplastin activity was obtained starting from muscular tissue with an age of 4–7 days.

EXAMPLE 4

The preparation according to Example 1 was repeated by extracting with a 150 mM phosphate buffer at 4° C. A preparation was then carried out by extracting with a phosphate buffer having a temperature of 50° C. Following the homogenisation, the temperature of the homogenate was 40° C. The other steps were carried out as described in Example 1. The thromboplastin activity obtained when the extraction temperature was increased was 34% higher than the activity obtained using a cold extraction.

EXAMPLE 5

An amount of 1000 g salmon was cut down at 4° C. and was then homogenised and extracted at 4° C. in 1000 ml of 150 mM phosphate buffer, pH 7.0. Otherwise, the process for the extraction and determination of the thromboplastin activity was carried out as described in Example 1. Following a centrifugation at 3200 g during 30 minutes at 0° C., the thromboplastin activity in the obtained supernatant was determined. With respect to bovine prothrombin (390 NIH-U/ml) the activity was 55%RTP; with respect to porcine prothrombin (242 NIH-U/ml) the activity was 45%RTP.

Comparable results were obtained when this process was applied to 1000 g herring. The obtained thromboplastin activity was 49%RTP with respect to bovine prothrombin, and 40%RTP with respect to porcine prothrombin.

What is claimed is:

1. A process for the preparation of thromboplastin from mammalian or fish muscle tissue comprising:

directly extracting a sample of mammalian or fish muscle tissue with an aqueous salt solution; and recovering thromboplastin in a liquid extract separated from the sample muscle tissue;

wherein, prior to extraction, the sample muscle tissue is aged 4–10 days after slaughter or the sample muscle tissue is vacuum packed and aged for 2 weeks after slaughter.

2. The process according to claim 1, wherein the aqueous salt solution is buffered to pH 6.0–7.5.

3. The process according to claim 1, wherein the sample muscle tissue is extracted with a physiological salt solution.

4. The process according to claim 1, wherein the physiological salt solution comprises a phosphate salt.

5. The process according to claim 1, wherein the aqueous salt solution has a temperature of 40° C.–50° C. during the extraction.

6. The process according to claim 1, wherein the sample muscle tissue is separated from the liquid extract by centrifugation.

* * * * *